| United States Patent [19] | [11] | 4,122,259 |
|---|---|---|
| Humber | [45] | Oct. 24, 1978 |

[54] 7β-[2-ARYL-2-(ETHERIFIED OXIMINO)ACETAMIDO]-3-N-SUBSTITUTED CARBAMOYLOXYMETHYLCEPH-3-EM-4-CARBOXYLIC ACIDS

[75] Inventor: David C. Humber, London, England

[73] Assignee: Glaxo Laboratories Limited, Greenford, England

[21] Appl. No.: 749,299

[22] Filed: Dec. 10, 1976

Related U.S. Application Data

[63] Continuation of Ser. No. 603,815, Aug. 12, 1975, abandoned.

[30] Foreign Application Priority Data

Aug. 23, 1974 [GB] United Kingdom ............... 37197/74

[51] Int. Cl.² ............................................ C07D 501/20
[52] U.S. Cl. ..................................... 544/22; 424/246; 544/16

[58] Field of Search ................ 260/243 C; 544/16, 22

[56] References Cited

U.S. PATENT DOCUMENTS 3,974,153  8/1976  Cook et al. ...................... 260/243 C Primary Examiner—Nicholas S. Rizzo
Attorney, Agent, or Firm—Bacon & Thomas

[57] ABSTRACT

Cephalosporin antibiotics in which the 7β-acylamido group is syn 2-aryl-2-(etherified imino) acetamido and in which the 3-position substituent is an alkyl-, alkenyl- etc. substituted carbamoyloxymethyl group exhibit high antibacterial activity against a broad range of gram positive and gram negative organisms, particularly high stability to β-lactamases produced by various organisms, and stability in vivo. The compounds are syn isomers or exist as mixtures of syn and anti isomers containing at least 90% of the syn isomer.

13 Claims, No Drawings

7β-[2-ARYL-2-(ETHERIFIED OXIMINO)ACETAMIDO]-3-N-SUBSTITUTED CARBAMOYLOXYMETHYLCEPH-3-EM-4-CARBOXYLIC ACIDS

This is a continuation, of application Ser. No. 603,815, filed Aug. 12, 1975, and now abandoned.

This invention is concerned with improvements in or relating to antibiotics of the cephalosporin series.

The cephalosporin compounds in this specification are named with reference to "cepham" after J. Amer. Chem. Soc., 1962, 84, 3400, the term "cephem" referring to the basic cepham structure with one double bond.

Many cephalosporin compounds possessing a degree of antibacterial activity are known in the art, these compounds possessing $\Delta^3$ unsaturation and ordinarily being substituted at the 3-position by a methyl or substituted methyl group and at the 7β-position by an acylamido group. It is now well recognised that the antibiotic properties of a particular ceph-3-em-4-carboxylic acid are predominantly controlled by the nature of both the 7β-acylamido group thereof and the 3-position substituent which the compound carries; considerable research has been undertaken to find combinations of such groups which will yield antibiotics with particular properties.

Cephalosporin antibiotics are widely used in the treatment of diseases caused by pathogenic bacteria in human beings and animals, for example in the treatment of diseases caused by bacteria which are resistant to other antibiotics such as penicillin compounds and in the treatment of penicillin-sensitive patients. In many applications it is desirable to employ a cephalosporin antibiotic which exhibits activity against both gram positive and gram negative microorganisms, and a significant amount of research has been directed to the development of improved broad spectrum cephalosporin antibiotics.

The practical utility of a significant number of known commercial and experimental cephalosporin antibiotics is limited by their relatively high susceptibility to the β-lactamases which are produced by many bacteria. A desirable property of a broad spectrum cephalosporin antibiotic is therefore that it should exhibit substantial resistance to β-lactamases, including those produced by gram negative microorganisms.

A further difficulty with many cephalosporin antibiotics intended for therapeutic applications is that they are subject to degradation in vivo. Thus a significant member of known cephalosporin antibiotics have been found to suffer the disadvantage that following administration they are deactivated, often rapidly, by enzymes (e.g. esterases) present in the body.

As a result of prolonged studies of numerous cephalosporin compounds we have now found a class of cephalosporin antibiotics having a particular combination of 7β-acylamido group and 3-position substituent which endows the compounds with good broad spectrum activity coupled with the above-described desiderata of high β-lactamase stability and good stability in vivo.

The present invention, therefore, provides antibiotic compounds of the general formula

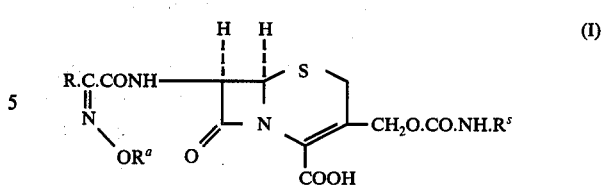

(where R represents a furyl, thienyl or phenyl group; $R^a$ represents a $C_1$-$C_4$ alkyl group, a $C_2$-$C_4$ alkenyl or alkynyl group, a $C_3$-$C_7$ cycloalkyl group or a phenyl group and $R^s$ represents a $C_1$-$C_4$ alkyl group, a $C_2$-$C_4$ alkenyl or alkynyl group, a $C_3$-$C_7$ cycloalkyl group, a benzyl group or a phenyl group) and non-toxic derivatives thereof, the compounds being syn isomers or existing as mixtures of syn and anti isomers containing at least 90% of the syn isomer. Most preferably the compounds are syn isomers essentially free from the corresponding anti isomers.

The compounds of the present invention are defined as having the syn (cis)isomeric form as regards the configuration of the group $OR^a$ with respect to the carboxamido group. In this specification the syn configuration is structurally defined thus

The syn configuration is assigned on the basis of the work of Ahmad and Spenser in Can. J. Chem 1961, 39, 1340.

The term "non-toxic" as applied to derivatives of the compounds of the invention means those derivatives which are physiologically acceptable in the dosage at which they are administered. Such derivatives may include, for example, salts, biologically acceptable esters, 1-oxides and solvates (especially hydrates).

Salts which may be formed, where applicable, from the compounds according to the invention include inorganic base salts such as alkali metal, e.g. sodium and potassium, alkaline earth metal e.g. calcium, and organic base, e.g. procaine, phenylethylbenzylamine, dibenzylethylenediamine, ethanolamine, diethanolamine, triethanolamine and N-methylglucosamine, salts. The salts may also be in the form of resinates, formed e.g. with a polystyrene resin or cross-linked polystyrene divinylbenzene copolymer resin containing amino or quaternary amino groups.

When R in the above formula I is a furyl group it may be fur-2-yl or fur-3-yl and where it is a thienyl group it may be thien-2-yl or thien-3-yl. Preferably the group R is a fur-2-yl group.

As indicated above, the group $R^a$ in formula I represents an alkyl group containing 1-4 carbon atoms e.g. a methyl or ethyl group; an alkenyl or alkynyl group containing 2-4 carbon atoms, e.g. vinyl, allyl or propargyl; a cycloalkyl group containing 3-7 carbon atoms, e.g. a cyclopentyl group; or a phenyl group.

The group $R^s$ in formula I may, where the definition so permits, be the same as or different from the group $R^a$. It may represent an alkyl group containing 1-4 carbon atoms e.g. a methyl or ethyl group; a $C_2$-$C_4$ alkenyl group e.g. a vinyl or allyl group; a $C_3$-$C_7$ cycloalkyl group e.g. cyclopentyl.

Preferably the group R is a fur-2-yl group and the group $R^a$ is a methyl group.

The antibiotic compounds of the invention are characterized by their high antibacterial activity against a range of gram-positive and gram-negative organisms, their particularly high stability to β-lactamases produced by various gram negative organisms, which properties may render them useful in the treatment of a variety of diseases caused by pathogenic bacteria in human beings and animals.

An important compound falling within general formula I by virtue of its broad spectrum antibiotic properties; stability in the presence of human serum; high stability to β-lactamases produced by a variety of organisms; and resistance to the action of mammalian esterases is (6R,7R)-7-[2-(fur-2-yl)-2-methoxyiminoacetamido]-3-N-methylcarbamoyloxymethyl-ceph-3-em-4-carboxylic acid (synisomer), having the formula

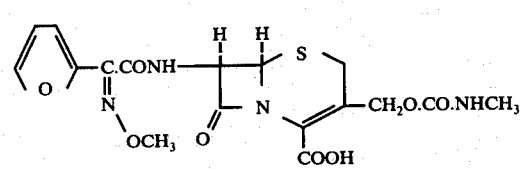

for example as its sodium or potassium salt.

The compounds according to the invention may be prepared by any convenient method.

According to one embodiment of the invention we provide a process for the preparation of an antibiotic compound of general formula I (as hereinbefore defined) and non-toxic derivatives thereof which comprises either (A) condensing a compound of the formula

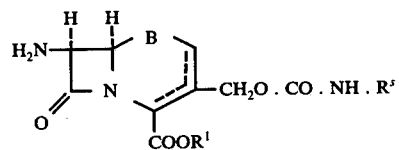

(wherein B is $>$ S or $>$ S $\rightarrow$ 0, $R^1$ is hydrogen or a carboxyl blocking group, $R^s$ has the above-defined meaning, and the dotted line bridging the 2-, 3- and 4-positions of formula (II) indicates that the compound may be a ceph-2-em or ceph-3-em compound) or an acid addition salt or N-silyl derivative thereof with an acylating agent corresponding to the acid:

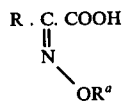

(wherein R and $R^a$ have the above-defined meanings or with an acylating agent corresponding to an acid which is a precursor for the acid (IV); or (B) reacting a compound of the formula

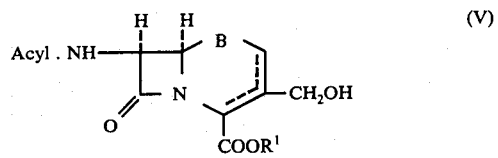

(wherein Acyl is the group

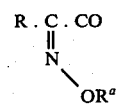

or a precursor therefor; B, $R^1$ and the dotted line have the above meanings) with an isocyanate of the formula $R^s$ NCO (wherein $R^s$ has the above defined meaning) whereafter, if necessary and desired in each instance, any of the following reactions (C), in any appropriate sequence, are carried out (i) conversion of a precursor for the desired

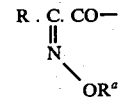

group into that said group, (ii) conversion of a $\Delta^2$ isomer into the desired $\Delta^3$ isomer, (iii) removal of any carboxyl blocking groups, and (iv) reduction of a compound in which B is $>$ S $\rightarrow$ 0 to form the desired B $=$ $>$ S compound; and (D) recovering the desired compound of formula (I), after separation of syn and anti isomers if necessary, and if desired after conversion of the compound to a non-toxic derivative thereof.

Where $R^1$ is a carboxyl blocking group it may be the residue of an ester-forming alcohol (aliphatic or araliphatic), phenol, silanol or stannanol or a symmetrical or mixed anhydride group derived from an appropriate acid.

Non-toxic derivatives of formula I may be formed in any convenient way. For example base salts may be formed by reaction of the cephalosporin acid with sodium or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example, with a peracid such as metaperiodic, peracetic, monoperphthalic or m-chloroperbenzoic acid or with t-butyl hypochlorite, conveniently in the presence of a weak base such as pyridine.

One may condense an acylating agent corresponding to the acid of formula (IV) with an amino compound of formula (III) where B and the dotted line have the above defined meanings and $R^1$ is hydrogen or a carboxyl blocking group or a derivative thereof, e.g., a salt such as a tosylate or an N-silyl derivative, the condensation optionally being effected in the presence of a condensation agent, and being followed, if necessary, by removal of a carboxyl blocking group $R^1$.

Compounds of formula I may thus be prepared by employing as the acylating agent an acid halide, particularly an acid chloride or bromide, corresponding to the acid (IV). Such acylations may be effected at temperatures of from −50° to +50° C, preferably −20° to +30° C. The acylation may be effected in aqueous or non-aqueous media.

Acylation with an acid halide may be effected in the presence of an acid binding agent, e.g., a tertiary amine such as triethylamine or dimethylaniline, an inorganic base such as calcium carbonate or sodium bicarbonate, or an oxirane, which serves to bind hydrogen halide liberated in the acylation reaction. Where an oxirane is employed for this purpose this is preferably a lower-1,2-alkylene oxide such as ethylene oxide or propylene oxide.

The free acid form of a compound of formula (IV) may itself be used as the acylating agent. Such acylations are desirably conducted in the presence of, for example, a carbodiimide such as N,N'-diethyl-, dipropyl- or diisopropylcarbodiimide, N,N'-dicyclohexylcarbodiimide, or N-ethyl-N'- dimethylaminopropylcarbodiimide; a carbonyl compound such as carbonyldiimidazole; or an isoxazolinium salt such as N-ethyl-5-phenylisoxazolinium-3'-sulphonate or N-t-butyl-5-methylisoxazolinium perchlorate. The condensation reaction is desirably effected in an anhydrous reaction medium, e.g. methylene chloride, dimethylformamide or acetonitrile.

Acylation may also be effected with other amide-forming derivatives of the free acid (IV) such as, for example, a symmetrical anhydride or mixed anhydride, e.g. with pivalic acid or formed with a haloformate such as a lower alkylhaloformate. The mixed or symmetrical anhydrides may be generated in situ. For example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluenesulphonic acid).

If desired, one can first prepare a compound of formula

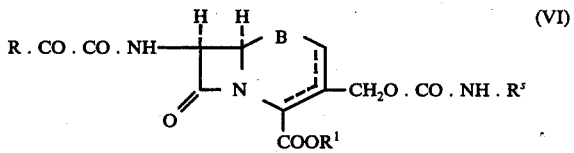

(where B, R, $R^1$, $R^s$ and the dotted line have the above defined meanings) and then effect reaction of the compound formula (V) with an etherified hydroxylamine of formula $R^a O.NH_2$ ($R^a$ having the above defined meaning), followed, if necessary, by removal of the group $R^1$. The reaction product may be separated to give the required syn isomer before or after removal of $R^1$.

The reaction of the 3-hydroxymethyl cephalosporin (V) with the isocyanate of formula $R^s.NCO$ (wherein $R^s$ has the above defined meaning) is preferably effected in the presence of a lower ($C_1-C_4$) trialkylamine. The reaction may be effected at a temperature in the range −50° to +105° C, conveniently from 0° to +25° C. The reaction may be effected in a substantially inert organic solvent eg. an N,N-disubstituted amide, a halogenated hydrocarbon or an ether. Reactions of this type are described for example in U.S. Pat. No. 3,355,452.

3-Hydroxymethyl starting material for use in the process of this embodiment of the invention may be prepared by, for example, the methods described in British Pat. No. 1,121,308, and Belgian Pat. No. 783,449.

As indicated above, starting materials of formula III may if desired be employed in the form of acid addition salts, e.g. with hydrochloric, hydrobromic, sulphuric, nitric, phosphoric, toluene-p-sulphonic or methane sulphonic acids.

Any blocking group substituting the 4-carboxy group of compounds of formula III, V or VI is desirably a group which may readily be split off at a later stage of a reaction sequence and advantageously is a group containing 1-20 carbon atoms. Suitable blocked carboxyl groups are well known in the art, a list of representative groups being included in our aforementioned Belgian Pat. No. 783,449. Preferred blocked carboxyl groups include aryl lower alkoxycarbonyl groups such as p-methoxybenzyloxycarbonyl, p-nitrobenzyloxy carbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically catalysed hydrolyses.

Where at the end of a given preparative sequence compounds are obtained wherein B is $> S \rightarrow 0$ and a compound is desired in which B is $> S$, conversion to a sulphide may for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50° C.

Where the resultant compound is a ceph-2-em-4-carboxylic ester the desired ceph-3-em compound may be obtained by treatment of the former with a base.

The antibiotic compounds according to the invention may be formulated for administration in any convenient way, by analogy with other antibiotics and the invention therefore, includes within its scope a pharmaceutical composition comprising an antibiotic compound of formula I or a non-toxic derivative e.g. salt or biologically acceptable ester thereof adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multidose containers with an added preservative. The compositions may take such forms as suspensions, solutions, emulsions in oily or aqueous vehicles, and may contain formulatory agents such as suspending, stabilising and/or dispersing agents. Alternatively the active ingredient may be in powder form for re-constitution with a suitable vehicle, e.g. sterile, pyrogen-free water before use.

For veterinary medicine the compositions may, for example, be formulated as intramammary preparations in ether long acting or quick-release bases.

In general the compositions may contain from 0.1% upwards, preferably from 10–60% of the active material; depending on the method of administration. Where the compositions comprise dosage units, each unit will preferably contain 50–1500 mg. of the active ingredient. The dosage as employed for adult human treatment will preferably range from 500 – 4000 mg. per day, depending on the route and frequency of administration.

The compounds according to the invention may be administered in combination with other compatible therapeutic agents such as antibiotics, for example penicillins, other cephalosporins or tetracyclines.

The following examples illustrate the invention. All temperatures are in ° C. Melting points were determined on a Kofler block for Examples 1–6; for Examples 7–13 melting points were determined in open-ended capillaries on a Mettler apparatus and take the form ($M_y^x$) where $x$ is the rate of heating in ° C per minute and $y$ is the insertion temperature. Rotations were measured in the temperature range 18°–24° C. Ultra-violet spectra were measured in pH6 phosphate buffer. Structures were also confirmed by infrared and proton magnetic resonance spectroscopy.

EXAMPLE 1

(6R,7R)-7-[2-(Fur-2-yl)-2-methoxyiminoacetamido]-3-N-phenylcarbamoyloxymethylceph-3-em-4-carboxylic Acid (syn isomer)

A solution of (6R,7R)-7-[2-(fur-2-yl)-2-methoxyiminoacetamido]-3-hydroxymethylceph-3-em-4-carboxylic acid (syn isomer) (1.00g) in N,N-dimethylformamide (20ml, purified by filtration through basic alumina) was cooled to 5° and was treated with triethylamine (0.73ml) and phenyl isocyanate (2.85ml). The reaction was stirred for 1 hour at 5° when the ice-bath was removed and stirring continued for 1.5 hours at ca. 20°. The solution was partitioned between aqueous sodium bicarbonate solution (3%, 100ml) and ethyl acetate (100ml). The layers were separated and the aqueous solution was washed with ethyl acetate (3×100ml), then covered with ethyl acetate (100ml) and acidified to pH 1.8 with concentrated hydrochloric acid.

The layers were separated and the aqueous layer extracted with further ethyl acetate (4×100ml). The combined organic extracts were washed with water (5×150ml) and saturated sodium chloride solution (100ml) and dried (MgSO$_4$), and the solvent was removed in vacuo to give a yellow froth which was triturated with ether (50ml) to give the title compound (905mg) $[\alpha]_D$ + 27° (c 1, DMSO) $\lambda^{pH6}$max 255nm ($\epsilon$ 23,500) and 270nm ($\epsilon$ 19,500)

EXAMPLE 2

Sodium (6R,7R)-7-[2-(Fur-2-yl)-2-methoxyiminoacetamido]-3-N-methylcarbamoyloxymethylceph-3-em-4-carboxylate(syn isomer)

Treatment of (6R,7R)-7-[2-(fur-2-yl)-2-methoxyiminoacetamido]-3-hydroxymethylceph-3-em-4-carboxylic acid (syn isomer) (1.525g) in N,N-dimethylformamide (60ml) with triethylamine (1.12ml), and methyl isocyanate (2.0ml) as in Example 1, gave (6R,7R)-7-[2-(fur-2-yl)-2-methoxyiminoacetamido]-3-N-methylcarbamoyloxymethylceph-3-em-4-carboxylic acid (syn isomer) (0.803g). Part of this (0.726g) was dissolved in acetone (2ml) and a solution of sodium DL-2-ethylhexanoate (1.66mmole) in acetone (1.6ml) was added and the solution refrigerated overnight. The product was filtered off, washed with chilled acetone and dried in vacuo to give the title compound (282mg) $[\alpha]_D$ + 59° (C 1,H$_2$O); $\lambda^{pH6}$max 274nm ($\epsilon$ 17,600)

EXAMPLE 3

(6R,7R)-3-(N-Ethylcarbamoyloxymethyl)-7-[2-(fur-2-yl)-2-methoxyiminoacetamido]ceph-3-em-4-carboxylic Acid (syn isomer)

Reaction of (6R,7R)-7-[2-(fur-2-yl)-2-methoxyiminoacetamido]-3-hydroxymethylceph-3-em-4-carboxylic acid (syn isomer) (1.54g) in N,N-dimethylformamide (60ml) with ethyl isocyanate (2.0ml) and triethylamine (1.12ml) as in Example 1 gave the title compound (622mg) $[\alpha]_D$ + 68° (C 1, DMSO); $\lambda^{pH6}$max 273nm ($\epsilon$ 16,350).

EXAMPLE 4

(6R,7R)-3-(N-t-Butylcarbamoyloxymethyl-7-[2-(fur-2-yl)-2-methoxyiminoacetamido]ceph-3-em-4-carboxylic Acid (syn isomer)

Reaction of (6R,7R)-7-[2-(fur-2-yl)-2-methoxyiminoacetamido]-3-hydroxymethylceph-3-em-4-carboxylic acid (syn isomer) (2.00g) in N,N-dimethylformamide (60ml) with t-butyl isocyanate (5.20g) and triethylamine (2.92ml) as in Example 1, gave the title compound (1.58g) $[\alpha]_D$ + 77° (c 1, DMSO); $\lambda^{pH6}$max 275nm ($\epsilon$ 16,400).

EXAMPLE 5

(6R,7R)-3-(N-Allylcarbamoyloxymethyl)-7-[2-(fur-2-yl)-2-methoxyiminoacetamido]ceph-3-em-4-carboxylic Acid (syn isomer)

Treatment of (6R,7R)-7-[2-(fur-2-yl)-2-methoxyiminoacetamido]-3-hydroxymethylceph-3-em-4-carboxylic acid (syn isomer) (2.00g) in N,N-dimethylformamide (100ml) with triethylamine (2.0ml) and allyl isocyanate (4.42g) as in Example 1, afforded the title compound (1.63g,) $[\alpha]_D$ +32°(c 1, 1,DMSO); $\lambda^{pH6}$max 274nm ($\epsilon$ 13,100).

EXAMPLE 6

(6R,7R)-7-[2-(Fur-2-yl)-2-methoxyiminoacetamido]-3-N-methylcarbamoyloxymethylceph-3-em-4-carboxylic Acid syn isomer)

A suspension of (6R,7R)-7-[2-(fur-2-yl)-2-methoxyiminoacetamido]-3-hydroxymethylceph-3-em-4-carboxylic acid (syn isomer) (1.00g) in dry dichloromethane (50 ml.) was treated with tri-n-butyl tin oxide (0.871 g) and stirred under nitrogen for 30 minutes at 21°, during which time the suspension dissolved. Methyl isocyanate (0.60 g., 10.50 mmole) was added, and stirring continued for a further 3 hours. Ethyl acetate (30 ml.) and water (30 ml.) were added and the dichloromethane removed in vacuo. The volume of ethyl acetate was made up to ca. 30 ml. and the pH of the solution adjusted to 8.5 with aqueous sodium bicarbonate solution. The aqueous solution was washed with ethyl acetate (3 × 30 ml.) then covered with further ethyl acetate (30 ml.) and adjusted to pH 1.9 with hydrochloric acid. The phases were separated and the aqueous phase extracted with further ethyl acetate (3 × 50 ml.). The combined ethyl acetate extracts were washed with saturated sodium chloride solution and dried (magnesium sulphate) and the solvent removed in vacuo to give the title carboxylic acid as an off-white froth (0.962 g); $[\alpha]_D$ + 47° (c 0.57, DMSO); $\lambda_{max}$ 273nm ($\epsilon$ 15, 450).

EXAMPLE 7

(6R,7R)-3-N-Cyclohexylcarbamoyloxymethyl-7-[2-methoxy 2-(fur-2-yl)acetamido]ceph-3-em-4-carboxylic Acid (syn isomer)

A suspension of (6R,7R)-3-hydroxymethyl-7-[2-methoxyimino-2-(fur-2-yl)acetamido]ceph-3-em-4-carboxylic acid (syn isomer) (1.00g) in dry benzene (50ml) under nitrogen was treated with tri-n-butyl tin oxide (0.870g) and solution was obtained after stirring for 30 minutes. Cyclohexyl isocyanate (1.318g) was added and stirring was continued for a further 3½ hours by which time the reaction was essentially complete.

Addition of water (50ml) to the reaction mixture caused the precipitation of dicyclohexylurea (which was filtered off). The benzene layer was separated, stirred and 0.1M hydrochloric acid (50ml) was added to give a white gelatinous precipitate which was filtered off. The precipitate was dissolved in aqueous sodium bicarbonate solution which was extracted with ethyl acetate (50ml). The aqueous phase was acidified with 2M-hydrochloric acid and extracted with ethyl acetate (2×80ml). The organic layer was washed with water (2×150ml), dried over magnesium sulphate and evaporated in vacuo to yield the title compound (396mg) as an off-white solid, m.p. ($M_{80}{}^2$) 162°, $[\alpha]_D^{20.5°}$ + 38.0°, (c. 1.03, dioxan), $\lambda_{max}$ (pH6 phosphate buffer) 274nm ($\epsilon$ 16,930).

EXAMPLE 8

(6R,7R)-3-N-n-Butylcarbamoyloxymethyl-7-[2-methoxyimino-2-(fur-2-yl)acetamido]ceph-3-em-4-carboxylic Acid (syn isomer)

A suspension of (6R,7R)-3-hydroxymethyl-7-[2-methoxyimino-2-(fur-2-yl)acetamido]ceph-3-em-4-carboxylic acid (syn isomer) (2.00g) in dry benzene (under nitrogen) was treated with tri-n-butyl tin oxide (1.74g) and solution was obtained after stirring for 1 hour. n-Butyl isocyanate (2.08g) was added and stirring was continued for a further 4 hours. Water (100ml) was added to the reaction mixture and the stirred separated benzene layer was treated with 0.1M hydrochloric acid (100ml) to deposit a gelatinous precipitate which was filtered off and dissolved in aqueous saturated sodium bicarbonate solution (100ml). After washing the aqueous solution with ethyl acetate (2×100ml) the aqueous phase was acidified with 2M hydrochloric acid under an ethyl acetate layer (100ml). The organic phase was separated and the aqueous layer was re-extracted with ethyl acetate (100ml). The combined organic extracts were washed with water (2×200ml), dried over magnesium sulphate and evaporated in vacuo to yield the title compound (1.124g) as a pale yellow solid, m.p.($M_{80}{}^2$) 149.6°, $[\alpha]_D^{20.5°}$ + 42.6° (c 1.03, DMSO), $\lambda_{max}$(pH6 phosphate buffer) 274nm ($\epsilon$ 16,960).

EXAMPLE 9

(6R,7R)-7-[2-Methoxyimino-2-(thien-2-yl)acetamido]-3-N-methylcarbamoyloxymethylceph-3-em-4-carboxylic Acid (syn isomer)

A solution of 2-methoxyimino-2-(thien-2-yl)acetic acid (syn isomer) (926mg) in dry dichloromethane (30ml) was cooled to ca 0° (under dry nitrogen).

This solution was stirred (at ca 0°) with triethylamine (0.7ml), oxalyl chloride (0.43ml) and dry N,N dimethylformamide (1 drop) for 1.25 hours during which time mild effervescence and decolouration occurred.

The solution was evaporated and dried in vacuo for 1.25 hours to give the corresponding acid chloride as off white crystals.

A solution of the acid chloride (ca 5mmole) in dry acetone (50ml) was added dropwise over 15 minutes (at ca 1° C) to a solution of (6R,7R)-7-amino-3-N-methylcarbamoyloxymethylceph-3-em-4-carboxylic acid (862mg) and sodium hydrogen carbonate (756mg) in water (60ml) and the reaction mixture was stirred for a further 1.25 hours by which time reaction was complete (by t.l.c.).

The solution (at ca pH 7) was washed with ethyl acetate (3×100ml) and the combined washings back-extracted with water (2×50ml).

The aqueous phase was layered with ethyl acetate (150ml) and acidified to pH 1.9 with concentrated hydrochloric acid. The aqueous phase was extracted with further ethyl acetate (2×100ml), the organic extracts were combined, washed with water (2×150ml), saturated brine (75ml), dried(magnesium sulphate) and evaporated in vacuo to give a semi-crystalline white solid (1.503g). Trituration of the crude product with ether (30ml) afforded the title compound (863mg), as a white solid m.p. ($M_{80}{}^2$) 144°, $[\alpha]_D^{22}$ +57.3° (c 1.14, DMSO), $\lambda_{max}$(pH6 phosphate buffer) 263nm ($\epsilon$ 16,300) with an inflection at 295nm ($\epsilon$ 10,650).

EXAMPLE 10

(6R,7R)-7-[2-Ethoxyimino-2-phenylacetamido]-3-N-methylcarbamoyloxymethyl-ceph-3-em-4-carboxylic Acid (syn isomer)

The method of preparation of this compound was similar to that described in Example 9 except that the acid chloride was made from 2-ethoxyimino-2-phenylacetic acid (syn isomer) (561mg) and the crude acid chloride was isolated as a yellow crystalline solid.

Dropwise addition of the acid chloride in dry acetone (28ml) to a solution of (6R,7R)-7-amino-3-N-methylcarbamoyloxymethylceph-3-em-4-carboxylic acid (500mg) and sodium hydrogen carbonate carbonate (439mg) in water (35ml) at ca 10° over 10 minutes and subsequent stirring at 5° to 10° for 3½ hours resulted in the acylation of the amino compound (as evidenced by tlc). The reaction mixture was then worked up in a manner substantially similar to that of Example 9 to afford the title compound (480mg) as a white powder m.p. ($M_{80}{}^2$) 138°, $[\alpha]_D^{22}$ +58.0° (c 1.0, DMSO), $\lambda_{max}$(pH6 phosphate buffer) 259nm ($\epsilon$ 20,150).

EXAMPLE 11

(6R,7R)-3-N-methylcarbamoyloxymethyl-7-[2-phenoxyimino-2-phenylacetamido]ceph-3-em-4-carboxylic acid (syn isomer)

The acid chloride of 2-phenoxyimino-2-phenylacetic acid (syn isomer) (700mg) was prepared in the same manner as that described in Example 9. The crude acid chloride was isolated as a pale brown gum.

A solution of this crude acid chloride in dry acetone (28ml) was added dropwise to a cooled (10°) solution of (6R,7R)-7-amino-3-N-methylcarbamoyloxymethylceph-3-em-4-carboxylic acid (500mg), water (35ml) and sodium hydrogen carbonate (439mg) over 10 minutes and reaction was complete (by tlc) after stirring for 3 hours at 5° to 10°. The reaction mixture was then worked up in a manner substantially similar to that of Example 9 to afford the title compound (453mg) as a white powder, m.p. ($M_{80}^2$) 165°, $[\alpha]_D^{24}$ +78.8° (c 1.23, DMSO), $\lambda_{max}$(pH6 phosphate buffer) 260nm ($\epsilon$ 20,050) with inflections at 265.5 nm ($\epsilon$ 18,685) and 282nm ($\epsilon$ 13,300).

EXAMPLE 12

(6R,7R)-7-[2-Cyclopentyloximino-2-(fur-2-yl)acetamido]-3-N-methylcarbamoyloxymethylceph-3-em-4-carboxylic Acid (syn isomer)

The precedure adopted for the preparation of the acid chloride was similar to that adopted for Example 9 except that 2-cyclopentyloximino-2-(fur-2-yl)acetic acid (syn isomer) (556mg) was employed as the starting acid. The acid chloride was subsequently isolated as a crystalline solid.

A solution of the above acid chloride in dry acetone (25ml) was added dropwise (at ca 10°) to a solution of (6R,7R)-7-amino-3-N-methylcarbamoyloxymethyl-ceph-3-em-4-carboxylic acid (500mg) and sodium hydrogen carbonate (439mg) in water (35ml) over a period of 10 minutes. After allowing the reaction to continue for 2 hours at 5° to 10° tlc indicated that reaction was complete. The reaction mixture was worked up in a manner substantially similar to that of Example 9 to afford the title compound (608mg) as a white powder, m.p. ($M_{80}^2$) 126°, $[\alpha]_D^{22}$ +68.5° (c 1.06, DMSO), $\lambda_{max}$(pH6 phosphate buffer) 276.5nm ($\epsilon$ 19,400).

EXAMPLE 13

(6R,7R)-3-N-methylcarbamoyloxymethyl-7-[2-methoxyimino-2-(fur-2-yl)acetamido]ceph-3-em-4-carboxylic Acid (syn isomer)

Preparation of the acid chloride was similar to the method described in Example 9 except that 2-methoxyimino-2-(fur-2-yl) acetic acid (syn isomer) (282mg) was used as the starting material. The acid chloride was isolated as off-white crystals.

A solution of the acid chloride (ca 1.67mmole) in dry acetone (17ml) was added dropwise (at ca 10°) to a solution of (6R,7R)-7-amino-3-N-methylcarbamoyloxymethylceph-3-em-4-carboxylic acid (287mg) and sodium hydrogen carbonate (252mg), in water (20ml) over 15 minutes. The mixture was maintained at 5° to 10° for 1hour by which time reaction was complete by tlc. The mixture was worked up in a similar manner to that described in Example 9 to yield the title compound (258mg) as a solid, m.p. ($M_{80}^2$) 159° $[\alpha]_D^{22}$ +58.9° (c 1.08, DMSO), $\lambda_{max}$(pH6 phosphate buffer) 273nm ($\epsilon$ 17,360) with inflections at 260.5 ($\epsilon$ 15,300) and 285nm ($\epsilon$ 15,825).

Preparation (6R,7R)-7-Amino-3-N-methylcarbamoyloxymethyl-ceph-3-em-4-carboxylic Acid.

A suspension of (6R,7R)-7-amino-3-hydroxymethyl-ceph-3-em-4-carboxylic acid (1.029g) in dry dichloromethane (50ml) was treated under nitrogen with triethylamine (0.436g) and with tri-n-butyl tin oxide (1.25g) and the mixture was stirred for 30min. Methylisocyanate (0.570g) in dry dichloromethane (5ml) was added and the reaction stirred at 22° for 4 hr. The insoluble material was filtered off and water (2ml) was added, the solution was cooled and the pH adjusted to 3.1 with formic acid. The resulting suspension was stirred for 30min at ca.5° and the precipitate filtered off, washed with cold water and dried in vacuo to give the title amino-acid (0.482g) $[\alpha]_D$ +34° (c 0.70, DMSO), $\lambda_{max}$(pH6 buffer) 263nm ($\epsilon$7,100), $\lambda_{inf}$246nm ($\epsilon$6,300).

I claim:

1. A compound selected from the group consisting of a cephalosporin antibiotic of the formula

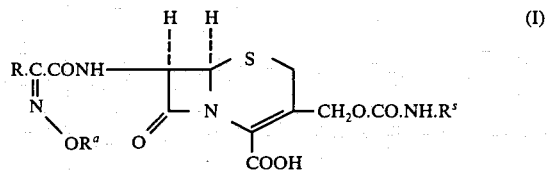

where R represents furyl, thienyl or phenyl; $R^a$ represents $C_1$–$C_4$ alkyl, $C_2$–$C_4$ alkenyl or alkynyl, $C_3$–$C_7$ cycloalkyl or phenyl and $R^s$ represents $C_1$–$C_4$ alkyl, $C_2$–$C_4$ alkenyl or alkynyl, $C_3$–$C_7$ cycloalkyl, benzyl or phenyl and a physiologically acceptable salt or oxide thereof.

2. The compound of claim 1 which is (6R,7R)-7-[2-(fur-2-yl)-2-methoxyiminoacetamido]-3-N-phenylcarbamoyloxymethylceph-3-em-4-carboxylic acid (syn isomer).

3. The compound of claim 1 which is (6R,7R)-7-[2-(fur-2-yl)-2-methoxyiminoacetamido]-3-N-methylcarbamoyloxymethylceph-3-em-4-carboxylic acid (syn isomer).

4. The compound of claim 1 which is sodium (6R,7R)-7-[2-(fur-2-yl)-2-methoxyiminoacetamido]-3-N-methylcarbamoyloxymethylceph-3-em-4-carboxylate (syn isomer).

5. The compound of claim 1 which is (6R,7R)-3-(N-ethylcarbamoyloxymethyl)-7-[2-(fur-2-yl)-2-methoxyiminoacetamido]ceph-3-em-4-carboxylic (syn isomer).

6. The compound of claim 1 which is (6R,7R)-3-(N-t-butylcarbamoyloxymethyl)-7-[2-(fur-2-yl)-2-methoxyiminoacetamido]ceph-3-em-4-carboxylic acid (syn isomer).

7. The compound of claim 1 which is (6R,7R)-3-(N-allylcarbamoyloxymethyl)-7-[2-(fur-2-yl)-2-methoxyiminoacetamido]ceph-3-em-4-carboxylic acid (syn isomer).

8. The compound of claim 1 which is (6R,7R)-3-(N-cyclohexylcarbamoyloxymethyl)-7-[2-(fur-2-yl)-2-methoxyiminoacetamido]ceph-3-em-4-carboxylic acid (syn isomer).

9. The compound of claim 1 which is (6R,7R)-3-(N-n-butylcarbamoyloxymethyl)-7-[2-(fur-2-yl)-2-methoxyiminoacetamido]ceph-3-em-4-carboxylic acid (syn isomer).

10. The compound of claim 1 which is (6R,7R)-7-[2-methoxyimino-2-(thien-2-yl)acetamido]-3-N-methylcarbamoyloxymethylceph-3-em-4-carboxylic acid (syn isomer).

11. The compound of claim 1 which is (6R,7R)-7-[2-ethoxyimino-2-phenylacetamido]-3-N-methylcarbamoyloxymethylceph-3-em-4-carboxylic acid (syn isomer).

12. The compound of claim 1 which is (6R,7R)-3-N-methylcarbamoyloxymethyl-7-[2-phenoxyimino-2-phenylacetamido]ceph-3-em-4-carboxylic acid (syn isomer).

13. The compound of claim 1 which is (6R,7R)-7-[2-cyclopentyloximino-2-(fur-2-yl)acetamido]-3-N-methylcarbamoyloxymethylceph-3-em-4-carboxylic acid (syn isomer).

* * * * *